United States Patent [19]

Ams et al.

[11] Patent Number: 4,866,526

[45] Date of Patent: Sep. 12, 1989

[54] VIDEO ENDOSCOPE WITH LIGHT INTENSITY REGULATION

[75] Inventors: Felix Ams, Kaempfelbach; Michael Voegele, Kaempfelbach-Ersingen, both of Fed. Rep. of Germany

[73] Assignee: Richard Wolf GmbH, Fed. Rep. of Germany

[21] Appl. No.: 223,028

[22] Filed: Jul. 22, 1988

[30] Foreign Application Priority Data

Jul. 25, 1987 [DE] Fed. Rep. of Germany ....... 3724761

[51] Int. Cl.⁴ .................... H04N 7/18; H04N 3/04; H04N 5/238; A61B 1/06
[52] U.S. Cl. .................................. 358/98; 358/202; 358/228; 128/6
[58] Field of Search .................. 358/98, 210, 202, 228; 128/4, 6

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 4,074,306 | 2/1978 | Kakinuma et al. | 358/1 |
| 4,253,447 | 3/1981 | Moore et al. | 128/6 |
| 4,261,344 | 4/1981 | Moore et al. | 128/6 |
| 4,301,790 | 11/1981 | Bol et al. | 128/6 |
| 4,331,403 | 5/1982 | Ohno | 128/6 |
| 4,509,508 | 4/1985 | Tsukaya | 128/6 |
| 4,631,582 | 12/1986 | Nagasaki et al. | 128/6 |
| 4,652,236 | 11/1986 | Fujimori et al. | 358/98 |
| 4,653,478 | 3/1987 | Nagasaki et al. | 128/6 |
| 4,713,683 | 12/1987 | Fujimori et al. | 358/98 |

FOREIGN PATENT DOCUMENTS

| | | |
|---|---|---|
| 0002220 | 1/1981 | European Pat. Off. |
| 0050834 | 5/1982 | European Pat. Off. |
| 0078957 | 5/1983 | European Pat. Off. |
| 1262502 | 3/1968 | Fed. Rep. of Germany |
| 3246239 | 6/1983 | Fed. Rep. of Germany |
| 3436057 | 5/1985 | Fed. Rep. of Germany |
| 3526993 | 2/1986 | Fed. Rep. of Germany |
| 3435598 | 6/1986 | Fed. Rep. of Germany |
| 3432018 | 7/1986 | Fed. Rep. of Germany |

Primary Examiner—John K. Peng
Attorney, Agent, or Firm—Hill, Van Santen, Steadman & Simpson

[57] ABSTRACT

A video endoscope having a semiconductor image converter which is incorporated in the endoscope and which receives the image of the object illuminated periodically by an illumination device with a sequence of partial colors, for example by using a filter wheel, and converts same into video signal components which correspond to partial color separations of the image and which are read successively and selectively separated according to partial colors into an intermediate store and are then read out simultaneously for the formation of an individual image and are processed for the representation of the image into television-compatible video signals, in which the lamp of the illumination device is pulsed with variable pulse amplitudes. The pulsed operation of the lamp is a function of the number of partial colors to be generated with an even-numbered multiple of the image repetition frequency, in which respect the light flux of the light pulses emitted by the lamp is variable as a function of the actual value of the respective amplitudes of the video signals, in order, in a predetermined range of regulations, to bring the actual value to a desired value. Arranged in the beam path of the lamp is an optical regulating element which undertakes a further regulation of the light intensity outside of the range of regulation.

15 Claims, 2 Drawing Sheets

VIDEO ENDOSCOPE WITH LIGHT INTENSITY REGULATION

BACKGROUND OF THE INVENTION

1. Field of the Invention

This invention relates to a video endoscope of the kind having a semiconductor image converter which is incorporated in the endoscope and which receives the image of the object illuminated periodically by an illumination device with a sequence of partial colors and converts the same into video signal components which correspond to partial color separations of the image, and which are written, successively and selectively separated according to partial colors, in an intermediate store and then read out simultaneously for the formation of a real-time individual image, and are processed for the representation of the individual image with a video processor into television-compatible video signals.

2. Description of the Prior Art

Modern endoscopes are semiconductor image converters to generate image signals. These generate, from the light falling onto their sensors (the light is usually conducted through a photoconductor to the endoscope) signals which correspond to the object that is to be inspected. These signals are, for the generation of video-compatible signals, subjected to a further processing and finally reproduced on a television monitor. To generate color pictures with such endoscopes it is known, for example, from DE-PS 34 35 598 to illuminate the object successively with the three primary colors, to store intermediately the respective color separations and then to read out simultaneously the three color separations in the next half image period or image period and compose the same into a television-compatible signal.

One problem with the use of such an endoscope consists in that, for objects having a different degree of reflection and/or at a different distance, the amount of light falling onto the image converter can lead to an overradiation or saturation of the image converter, or is no longer sufficient to generate a good television picture if it is too slight.

The endoscope arrangement disclosed in DE-PS 34 32 018 proposes for solving this problem, an automatic brightness regulation system working in a purely electronic manner, through the regulation of the voltage, applied to the light source emitting the light as a function of the result of the integration of the processed RGB-signals by the semiconductor image converter. However, it has been shown that electronic regulation alone does not achieve the high dynamic of the light intensity necessary for a good illumination of the object, to be inspected, at various object distances.

SUMMARY OF THE INVENTION

The main object of the present invention, is therefore, to develop further a video endoscope of the kind referred to hereinabove in such a way that the light intensity is so regulated as a function of the inspected object with adequate dynamics that the semiconductor image converter is not overirradiated or saturated while at all time an optimum video image is produced.

This object is achieved in accordance with the principles of the present invention in a video endoscope having a semiconductor image converter which is incorporated in the endoscope and which receives the image of the object illuminated periodically by an illumination device with a sequence of partial colors and converts same into video signal components which correspond to partial color separations of the image, and which are written successively and selectively separated according to partial colors in an intermediate store and then read out simultaneously for the formation of a real-time individual image, and are processed for the representation of the individual image with a video processor into television-compatible video signals, the lamp of the illumination device being operated pulsewise and with variable pulse amplitudes, namely as a function of the number of partial colors to be produced with an even-numbered multiple of the image repetition frequency. The light flux of the light pulses emitted by the same lamp is variable as a function of the actual value of the respective amplitudes of the video signal, in order, in a predetermined range of regulation, to bring the same actual value to a desired nominal value. Arranged in the beam path of the lamp is an optical regulating element, such as a diaphragm or a neutral or grey wedge filter, which undertakes a further regulation of the light intensity as soon as the aforesaid range of regulation is departed from.

Preferably, the said lamp is operated with idling current during the intervals between the light pulses.

In addition to achieving the main object of the invention, in a preferred embodiment by the combined regulation of the light flux through an electronic control of the voltage at the lamp and through an electronic control of the voltage at the lamp and through a mechanical control of an optical regulating element in the beam path of the light, the video endoscope has the advantage that, through the pulsewise operation of the lamp, the light yield thereof is considerably higher than in continuous operation, whereby, in combination with the two-stage regulation, the dynamics of the light flux are raised.

The actual value of the video signal may be supplied to a regulating circuit in which this actual value is compared with an adjustable desired value of the video signal. If deviations between both values occur, a first signal is generated and is transmitted to a lamp control to readjust the intensity of the light pulses in the sense of a linear amplification or weakening, the amplitude ratios of the light pulses in relation to one another being maintained, for the purpose of compensating for the regulation deviation. The regulating circuit generates a second signal for the adjustment of the optical regulating element if the compensation is not achievable by the lamp control.

Preferably, a diaphragm used as an optical regulating element and is controlled by a diaphragm motor which is controlled in two stages by an electrical diaphragm control by the aforementioned second signal of the regulating circuit, namely upon a large regulation deviation at a higher speed and upon a small regulation deviation at a lower speed.

Preferably, the motor drive of the filter wheel, provided for the sequential illumination of the object with the three primary colors, is synchronized by the video processor. Preferably, the partial colors for the illumination of the object are produced with the filter wheel and the filter wheel is driven electrically by a direct-current motor and is equipped with filters which, when the filter wheel is rotating, can be brought successively and periodically into the beam path of the lamp. The speed and phase relationship of the direct-current motor in respect to the corresponding partial color are controlled in synchronism with the repetition frequency determined by the video processor. The video processor may control the operation of the image converter with synchronization signals, with the video processor developing, as a function of and in synchronism with these synchronization signals, control pulses for the lamp operation, and for the motor if the filter wheel is used. In this way the quartz-accurate synchronization of several vision pick-up devices is made possible.

DESCRIPTION OF THE DRAWINGS

In order that the invention may be more readily understood, an embodiment thereof will now be described, by way of example, with reference to the accompanying drawings, in which.

DESCRIPTION OF THE PREFERRED EMBODIMENTS

Figure 1:
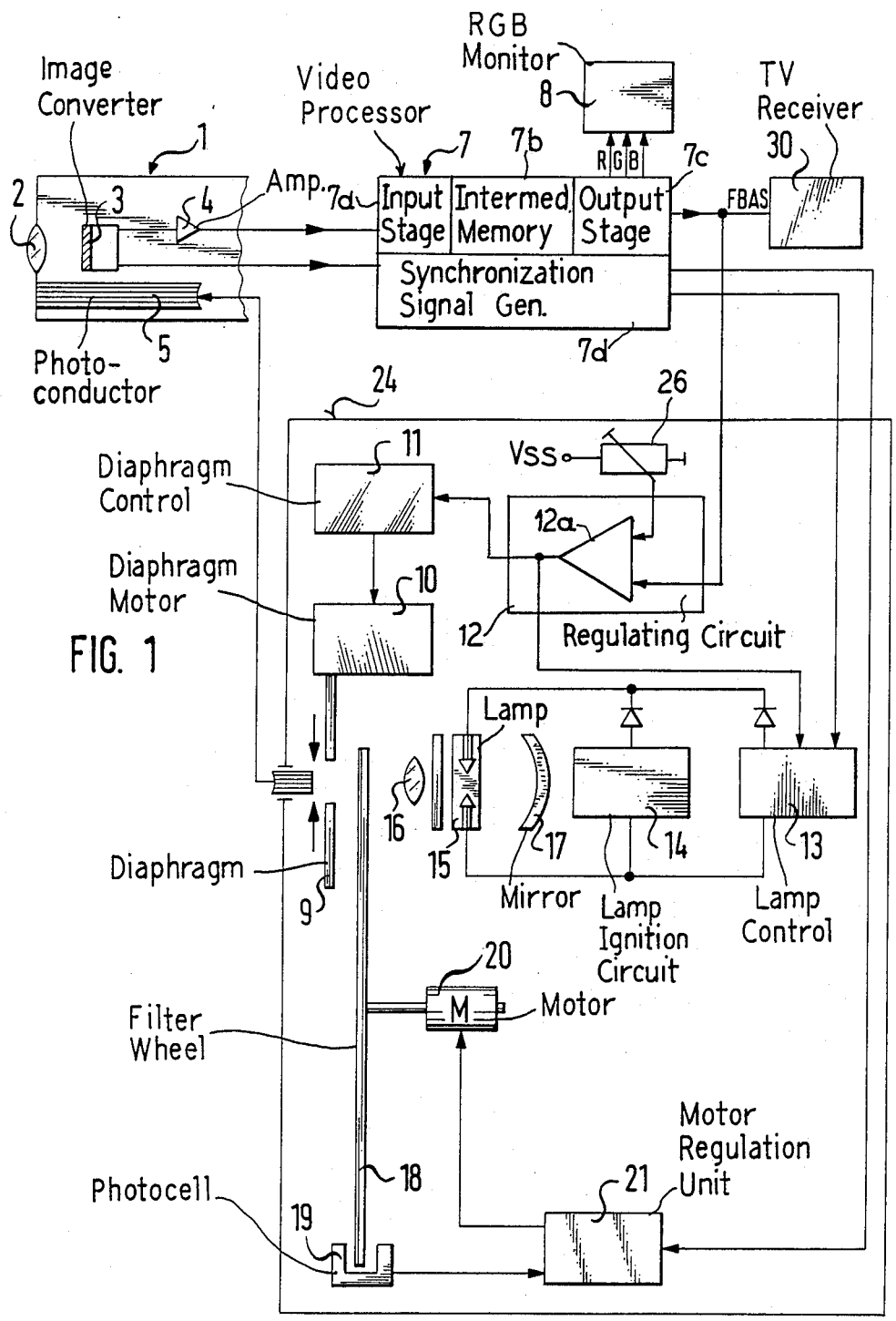
FIG. 1 is a block wiring diagram of a video endoscope constructed in accordance with the principles of the present invention.

Reproduced in the exemplified embodiment, shown in FIG. 1, of the endoscope is a reproduction of an object, illumination by a light source 24, onto the surface of a miniaturized semiconductor image converter 3. The image converter 3 is positioned in the end region of the endoscope 1 with an objective lens 2, lying therebefore, for the focusing of the image. It serves for converting the object reproduction into electrical signals which are processed by an amplifier 4 and a video processor 7 into television-compatible signals These are conducted as RGB-signals, generated in a video processor 7, onto an RGB monitor 8, or as similarly generated FBAS signals onto a television receiver 30, where they are displayed.

In the arrangement shown in FIG. 1, a light source designed as a rare-gas arc lamp 15 serves to generate a light flux necessary for the viewing of the object A parabolic mirror 17 and a collecting lens 16 increase the usable amount of light. The light supply to the endoscope 2 is effected by a photoconductor 5. A filter wheel 18 with the primary colors red, green, blue lies in the beam path between the lamp 15 and the entry to the photoconductor 5. The filter wheel 18 is rotated by a motor 20, after generation of each color separation, by such an angle that the next filter for the generation of the next color separation lies in the beam path.

Serving for the synchronization of the motor in this exemplified embodiment is a fork light barrier 19 and the motor regulation unit 21.

Arranged in the beam path between the filter wheel 18 and the entry to the photoconductor 5 is an electrically actuated diaphragm with which the amount of light incident on the object is controlled. The diaphragm 9 is controlled by a diaphragm control 11 which operates a diaphragm motor 10 such that the FBAS signal at the television receiver 30 is leveled to a desired value which is adjustable by an adjuster 26, the regulation being undertaken by a regulating circuit 12.

The regulating circuit 12 includes a comparator 12a which generates two signals upon the occurrence regulation deviations between actual and desired value: A first signal for a lamp control 13 which increases the light intensity of the rare-gas arc lamp 15 in synchronism with the generation of the individual color separations, (in such a way that the intensity of the light pulses is readjusted in the sense of a linear amplification or weakening while retaining the amplitude ratios of the light pulses in relation to one another for compensating for the regulation deviation), and a second signal which is conducted to the diaphragm control 11.

The second signal for the diaphragm control 11 is generated only when the lamp control 13 is no longer able to regulate the FBAS signal to the desired value. The combination of the regulation of the light flux by the varying of the light intensity of the map 15 and by the adjusting of the diaphragm 9 offers the advantage of a very accurate electronic regulation within tight limits and very high dynamics of the light intensity (typically 1 to 100%).

Figure 2:
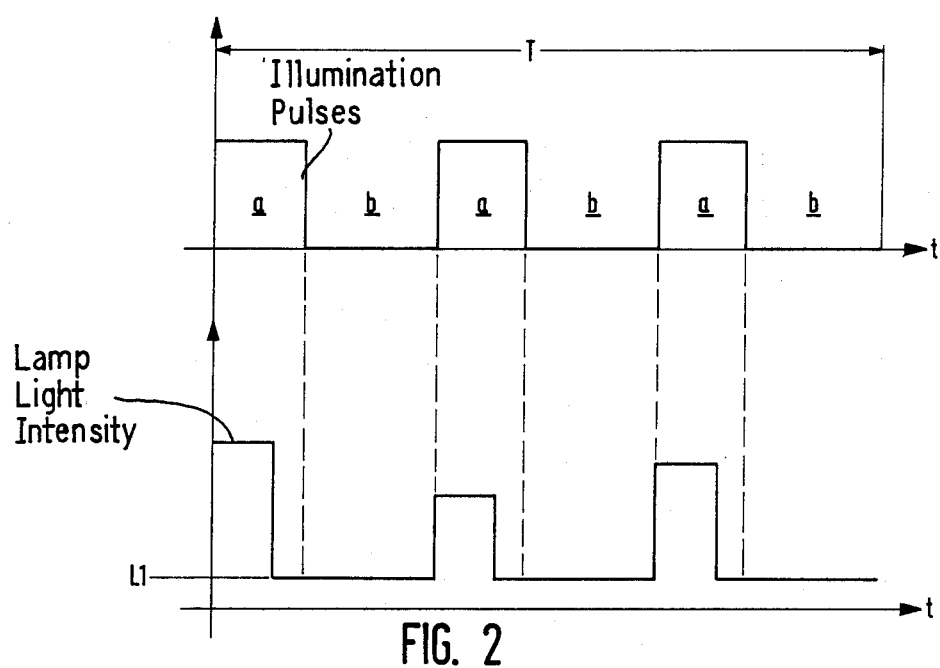
FIG. 2 is a cycle diagram which shows the temporal relation between the illuminating of the object and the storage of the signals generated by the image converter, and the control of the lamp.

The temporal relation between the illuminations of the object with respectively one color, the storing of the signals and the control of the lamp 15 are shown in FIG. 2.

Shown in the upper part of FIG. 2 are the illumination pulses which occur during an image period T and which are supplied by the video processor 7 as control signals to the semiconductor image converter 3. Their number corresponds to the number of partial colors to be generated, in the present exemplified embodiment corresponding to the three primary colors. Each illumination phase a is followed by a storage phase b, during which the signals generated by the image converter 3 are entered by an input stage 7a of the video processor 7 in an intermediate memory 7b. *In the case of some image converters no light may fall on the sensor surface thereof during the reading of the image content, since this would lead to a blurring of the image. This is achieved, in the exemplified embodiment, during the reading phase by the use of the filter wheel 18, which continues to be rotated during this phase, so that the filter wheel 18 (FIG. 3 then does not lie in the beam path. After an image period the stored partial color images or color separations are read out jointly and processed in an output stage 7c of the video processor 7 into a full-color image.*

As shown in the lower part of FIG. 2, the lamp 15 is higher valued during each illumination time starting from a basic light intensity L1 by the lamp control 13. The rare-gas arc lamp 15 used in the exemplified embodiment is ignited once during switching-on by the ignition circuit 14 and after that burns constantly with a certain quiescent current, from which there results the basic light intensity shown in FIG. 2. During the integration time of the semiconductor image converter 3, the light intensity is increased in a pulse-like manner in amplitude, the amplitude depending on the first signal generated in the regulating circuit 12.

The light modulation is effected accordingly with an even-numbered multiple of the image repetition frequency (50 Hertz in the case of CCIR, 60 Hertz in the case of EIA) in synchronism with the illumination and storage cycle.

Thus the overall power consumption is lowered as compared with use with unmodulated light with the same image brightness. Furthermore a higher light yield results, since the lamp in pulse operation can supply a multiple of the light yield that would be the case in continuous operation, since the pulsed operation it can accommodate considerably higher currents. Thus the image converter 3 can be acted upon during the integration time with a considerably higher light intensity than in the case of a continuous operation of the lamp. In addition, this operation of the lamp offers the possibility of selecting the pulse amplitude during the individual color separations in a differently high manner and thus of compensating for the transmission differences of the individual color filters of the filter wheel 18 and the spectral sensitivity of the image converter 3. Thus the result is achieved that, in the case of a while image original copy, the image converter 3 is illuminated uniformly in all the color separations, so that the same signal-to-noise ratio exists for all of them.

The motor-controlled diaphragm 9 is preferably designed in two-stages in the sense that with a large regulation deviation the diaphragm is operated at a higher speed and with a small regulation deviation it is operated at a lower speed. In this way, the inertia of the light regulation is reduced and the tendency towards oscillations of the regulating circuit is suppressed, which would be manifested by periodic opening and shutting of the diaphragm with the same object distance, by virtue of a too-rapid motor drive with small hysteresis. Instead of a mechanical diaphragm, a grey wedge coarse filter can be used, the position of which in the beam path of the light is adjusted.

Figure 3:
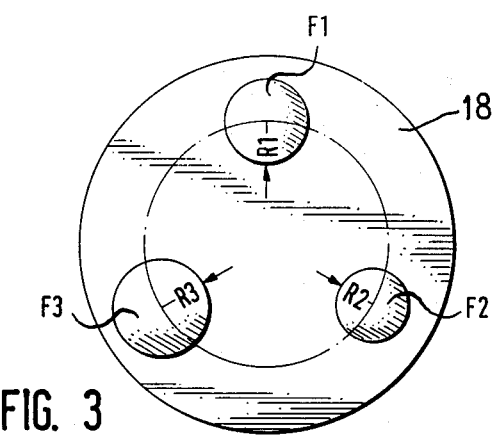
FIG. 3 is a top plan view of a filter wheel for producing the differently-colored separations of the object that is to be viewed.

FIG. 3 shows a typical filter wheel with three color filters F, which, with the filter wheel rotating, are brought successively and periodically into the beam path of the lamp. The radii of the filters R1, R2, R3 are not necessarily the same. Different radii can be provided for an adaptation of the amount of light passing through to the sensor characteristic of the image converter 3.

The filters can also differ in the color from the primary colors red, green, blue. For example, the colors white, cyan and yellow can be used This has the advantage of a higher spurious signal spacing since the spectral transmission forward regions of this filter combination are greater.

The motor driving the filter wheel 18 is, in accordance with a further development of the invention, a direct-current motor. Its speed and phase relationship with respect to the corresponding partial color are controlled in synchronism with the repetition frequency determined by the video processor 7. The use of a direct-current motor thus simplifies the control, saves space and reduces the production costs.

The conception of the present endoscope allows, moreover, the video processor 7 can include a synchronization signal generator 7d to take over the entire synchronization both of the image pick-up and of the control pulses for the lamp operation, and of the motor if the filter wheel is used. This makes possible the synchronization of several image pick-up devices. If several image pick-up devices are connected together it is necessary for the devices to be synchronized in a master-slave operation. In this respect the video endoscope can be operated both as master, i.e., as timing generator, and as slave, in which respect a then different image pick-up apparatus takes over the synchronization. As a result synchronization is, in addition, no longer dependent upon mechanical parameters, since it is generated in a quartz-accurate manner in the video processor. Thus the fork light barriers used in known endoscopes for the synchronization of the filter wheel are avoided.

Although modifications and changes may be suggested by those skilled in the art it is the intention of the inventors to embody within the patent warranted hereon all changes and modifications as reasonably and properly come within the scope of their contribution to the art.

We claim as our invention:

1. A video endoscope for viewing an object comprising:
   means for illuminating said object with a light sequence of partial colors in a beam path including said object, the illumination of said object forming a light image of said object;
   means for converting, at an image repetition frequency, said light image into video signal components corresponding to partial color separations of said light image, said video signal components having respective actual amplitudes;
   means for generating a real-time image of said object from said video signal components;
   means for pulsing said means for illuminating for generating light pulses of variable amplitude as a function of the amplitudes of said video signal components, and at an even numbered multiple of said image repetition frequency;
   control means connected to said means for generating said means for pulsing for varying said amplitude of said light pulses for maintaining deviations between said actual amplitude and said variable amplitude within a selected regulation range; and
   optical means in said beam path connected to said control means for optically regulating said variable amplitudes if said deviations exceed said selected regulation range.

2. A video endoscope as claimed in claim 1, wherein said means for generating a real-time image comprises:
   an intermediate memory;
   means for successively entering said video signal components into said memory; and
   means for reading the signals stored in said memory out of said memory to form said real-time image of said object.

3. A video endoscope as claimed in claim 1, further comprising:
   means for visually displaying said real-time image of said object.

4. A video endoscope as claimed in claim 1, wherein said optical means is a diaphragm having an aperture variable in size by said control means.

5. A video endoscope as claimed in claim 1, wherein said optical means is a wedge filter.

6. A video endoscope as claimed in claim 1, further comprising means for supplying said means for illuminating with an idling current during the intervals between said light pulses.

7. A video endoscope as claimed in claim 1, wherein said control means includes means for comparing said actual amplitudes with said variable amplitudes, said comparator generating a first signal supplied to said means for illuminating to vary the intensity of said light sequence and generating a second signal supplied to said optical means for controlling said optical means if said deviations exceed said selected regulation range.

8. A video endoscope as claimed in claim 7, wherein said optical means comprises:
   a diaphragm having an adjustable aperture;
   a motor connected to said diaphragm for changing the size of said aperture; and a motor regulation means for controlling the speed of said motor in response to said second signal from said comparator, said motor regulation means operating said motor at a speed which increases with the magnitude of said second signal.

9. A video endoscope as claimed in claim 1, wherein said means for illuminating said object includes a filter wheel having a plurality of filters therein for producing said partial colors, and a motor for rotating said filter wheel in said beam path to successively and periodically bring said filters into said beam path.

10. A video endoscope as claimed in claim 9, wherein said motor is a direct current motor operating at a speed and phase relative to each partial color, and further comprising means for synchronizing said speed and phase of said motor with said image repetition frequency.

11. A video endoscope as claimed in claim 10, wherein said means for synchronizing is means in said for generating a real-time image for generating synchronization signals for controlling said means for converting, said direct current motor and said means for pulsing said means for illuminating.

12. A video endoscope for viewing an object comprising:
    means for illuminating said object with a pulsed sequence of partial colors, the pulses in said sequence having variable amplitudes and forming a light image of said object;
    means for converting said light image into video signal components corresponding to partial color separations of said light image, said video signal components having respective actual amplitudes;
    means for comparing said actual amplitudes of said video signal components with said variable amplitudes of said partial color pulses and measuring the difference therebetween to generate a first control signal as long as said difference is within a selected regulation range, and to generate a second control signal if said difference exceeds said regulation range;
    means for controlling said means for illuminating to adjust said variable amplitudes of said partial colors based on said first signal to maintain said actual amplitudes of said video signal components at a selected level; and
    optical means in said beam path connected to said means for comparing to optically regulate said amplitudes of said partial color pulses in response to said second control signal.

13. A video endoscope as claimed in claim 12, wherein said optical means comprises:
    an adjustable diaphragm having an aperture in said beam path; and
    motor means for operating said diaphragm in response to said second control signal to change the size of said aperture.

14. A video endoscope as claimed in claim 13, further comprising means for regulating said motor means to operate said motor means at a speed which increases with the magnitude of said second control signal.

15. A method for operating a video endoscope for viewing an object comprising the steps of:
    illuminating said object with a pulsed light sequence of partial colors, the partial color pulses having variable amplitudes and forming a light image of said object;
    converting said light image of said object into video signal components corresponding to partial color separations of said light image, said video signal components having respective actual amplitudes;
    comparing the amplitudes of said partial color pulses with the actual amplitudes of said video signal components and generating a first control signal if the difference between said partial color amplitudes and said video signal component amplitudes are within a predetermined regulation range and generating a second control signal if said deviations exceed said regulation range;
    controlling the intensity of the illumination of said object using said first control signal to electrically vary the amplitudes of said partial color pulses; and
    controlling the illumination of said object using said second control signal to optically vary the amplitudes of said partial color pulses.

* * * * *